United States Patent [19]

Siegfried, II et al.

[11] Patent Number: 5,251,479
[45] Date of Patent: Oct. 12, 1993

[54] DOWNHOLE WELLBORE TOOL FOR MEASURING FLOW PARAMETERS

[75] Inventors: Robert W. Siegfried, II, Richardson; Keith W. Katahara, Allen, both of Tex.

[73] Assignee: Atlantic Richfield Company, Los Angeles, Calif.

[21] Appl. No.: 770,261

[22] Filed: Oct. 3, 1991

[51] Int. Cl.$^5$ .................. E21B 21/08; E21B 47/10; G01N 27/00; G01N 33/26
[52] U.S. Cl. .................................... 73/155; 73/19.10
[58] Field of Search ............... 73/861.05, 19.01, 19.10, 73/151, 154, 155

[56] References Cited

U.S. PATENT DOCUMENTS

| | | | |
|---|---|---|---|
| 3,176,304 | 3/1965 | Peters et al. | 73/155 |
| 3,279,249 | 10/1966 | Tocanne | 73/155 |
| 3,745,822 | 7/1973 | Pierce et al. | 73/154 |
| 4,109,717 | 8/1978 | Cooke, Jr. | 73/154 |
| 4,765,183 | 8/1988 | Coury | 73/154 |
| 4,811,598 | 3/1989 | Dillier et al. | 73/154 |
| 4,928,758 | 5/1990 | Siegfried | 73/155 |
| 4,947,683 | 8/1990 | Minear et al. | 73/155 |

FOREIGN PATENT DOCUMENTS 0026088 2/1984 Japan .......................... 73/861.05

Primary Examiner—Hezron E. Williams
Assistant Examiner—George M. Dombroske
Attorney, Agent, or Firm—Drude Faulconer

[57] ABSTRACT

A tool which is capable of measuring parameters of a multi-phase flowstream without substantially restricting the flow in the wellbore is disclosed. The tool is comprised of a plurality of extendable arms which are radially spaced around and pivotably mounted in a housing so that each arm is extendable from the housing into the flowstream in the wellbore. Various types of sensors, e.g. flow sensors, capacitance sensors, temperature sensors, etc., can be used either alone or in combination which are carried at or near the outer ends of each of the arms whereby the sensors will be deployed from the housing into the flowstream by the arms without substantially restricting the flowstream through the wellbore.

4 Claims, 2 Drawing Sheets

DOWNHOLE WELLBORE TOOL FOR MEASURING FLOW PARAMETERS

DESCRIPTION

1. Technical Field

The present invention relates to a downhole wellbore tool for measuring flow parameters and in one of its preferred aspects relates to a downhole tool which is positioned in a wellbore and which includes a plurality of sensing means which are extendable directly into the well flow to thereby measure the downhole flow parameters within the wellbore without substantially restricting or redirecting the flow.

2. Background Art

Surface measurements of the flow from a well have generally proved inadequate to effectively evaluate the downhole production and/or injection flow profiles of that well. To obtain the more accurate measurements needed for these profiles, several different types of tools have been developed or proposed which are lowered into the wellbore to make measurements of certain downhole flow parameters, e.g. velocities, at various depths in the well. Two of the better known of these tools are the "continuous spinner flowmeter" and the "diverting or basket flowmeter". For a good general description of these types of flowmeters, see "A New Flowmeter for Production Logging and Well Testing", G. E. Piers et al, SPE 16819, 62nd Annual Tech Conf. of Society of Petroleum Engineers, Dallas, Tex., Sep. 27-30, 1987 and "Production Logging-The Key to Optimum Well Performance", R. T. Wade et al, JOURNAL OF PETROLEUM TECHNOLOGY, February, 1965, pps.137-164.

In both types of flowmeters mentioned above, the flow velocity is determined from the rate of .e rotation of a propeller-type impeller (spinner) which is positioned in and powered by the flow stream. In the continuous spinner flowmeter (both conventional and fullbore), the impeller or spinner is situated at the lower end of the logging tool where it is exposed directly to the full flow stream. Inhomogeneities in the flow patterns for multi-phase flow, especially in wells deviated more than about 8°, render data from a continuous spinner flowmeter extremely difficult if not impossible to interpret even though such conditions are common. For example, in multi-phase flow in a deviated well, the flow can be stratified or there may be fall-back in which the heavier phases sometimes flow down rather than up. That is, downflow often occurs along the lower portion of the well, even though the net flow of both phases is up. Under these conditions, a spinner positioned along the lower side of the wellbore, or sometimes even if centered, may indicate flow in a direction opposite to that which is actually occurring.

Diverting flowmeters of the packer or basket types are designed to alleviate the problems encountered by the continuous spinner flowmeters by channeling the flow to an impeller which is positioned within the housing of the logging tool. At the higher flow velocities resulting from the diversion of the entire wellbore flow through a relatively small passage in the tool housing, severe flow inhomogeneities do not develop as readily and the revolutions per minute (RPMs) of the impeller are a far superior indication of total flow velocity Unfortunately, however, diverting flowmeters suffer from significant limitations. Unlike the continuous spinner flowmeters, diverting flowmeters must be stationary in the wellbore while a reading or measurement is made. Thus, flow readings are obtained only at discrete depths in the well, making the precise location of fluid entries or exits more difficult to resolve within a reasonable logging time span, as compared to the results from a continuous logging measurement. In addition, diverting flowmeters are limited as to the maximum flow rate that may be measured. At high flow rates, the pressure drop associated with the flow of the wellbore fluid through the narrow passage in the housing of the logging tool is sufficient to force the tool from its desired vertical position within the well. For example, the basket flowmeter normally can not be used in wells having flows greater than about 3500 barrels per day. Further, diverter flowmeters also tend to be mechanically unreliable while basket-type diverters often leak.

Another tool which has been proposed for measuring downhole flow parameters is disclosed in U.S. Pat. No. 4,928,758. This tool has a sleeve which is expanded to form an annulus between the sleeve and the wall of the wellbore. This annulus forms a restrictive passage through which all of the flow in the wellbore is directed. Means for measuring the flow parameters are carried by the sleeve and are positioned in the annulus when the sleeve is expanded. While this tool provides measurements which are useful in interpreting downhole flow parameters, these measurements are complicated by the fact that they are based on artificial flowrates through a restrictive passage (i.e. annulus) rather than the normal flowrates in the wellbore.

Therefore, certain benefits should result from being able to measure the flow parameters in a wellbore under conditions as close as possible to the actual flow conditions which exist in the wellbore at the point at which the measurements are taken.

DISCLOSURE OF THE INVENTION

The present invention provides a tool which is capable of measuring multi-phase flow parameters of a multi-phase flowstream without substantially restricting the flow in the wellbore or directing it through a restrictive flowpath. The present tool is particularly useful in deviated and horizontal wells as well as vertical wells. Unlike many present wellbore flowmeters which provide only point flow measurements for low flow rates, the present tool is capable of providing a continuous measurement over a wide range of practical flow rates which are normally expected to be encountered in a typical logging operation. In addition, the tool can be operated to provide data as to downhole flow inhomogeneities which can be useful in the interpretation of data from other types of production logging tools.

More specifically, the present tool is adapted to be positioned and operated by a "wire-line" and is comprised of a housing having an electronic section and a sensor section which, in turn, is comprised of a plurality of extendable, elongated arms which are radially spaced around and pivotably mounted in the housing so that each arm is extendable from the housing into the flowstream in the wellbore. A wide variety of means can be used to move the arms between their relative retracted and extended positions, e.g. a motor-driven worm gear. The extension of the arms do not substantially alter or restrict the flowstream as it flows pass the tool.

A variety of sensors are carried at or near the outer ends of each of the arms whereby the sensors will be deployed from the housing into the flowstream without substantially restricting the flowstream through the wellbore. Each sensor will measure a property or parameter of the flow at its respective point in the wellbore. From these measurements, it is possible to construct a cross-sectional map or image at each instant of the measured fluid property.

Various types of sensors can be used either alone or in combination on each arm, e.g. flow sensors for measuring flow velocities, sensors for measuring the capacitance of the fluids in the wellbore to determine the composition of the fluids, thermal probes for measuring the temperatures of the fluids, and combinations thereof.

BRIEF DESCRIPTION OF THE DRAWINGS

The actual construction, operation, and apparent advantages of the present invention will be better understood by referring to the drawings in which like numerals identify like parts and in which.

BEST MODE FOR CARRYING OUT THE INVENTION

Figure 1:
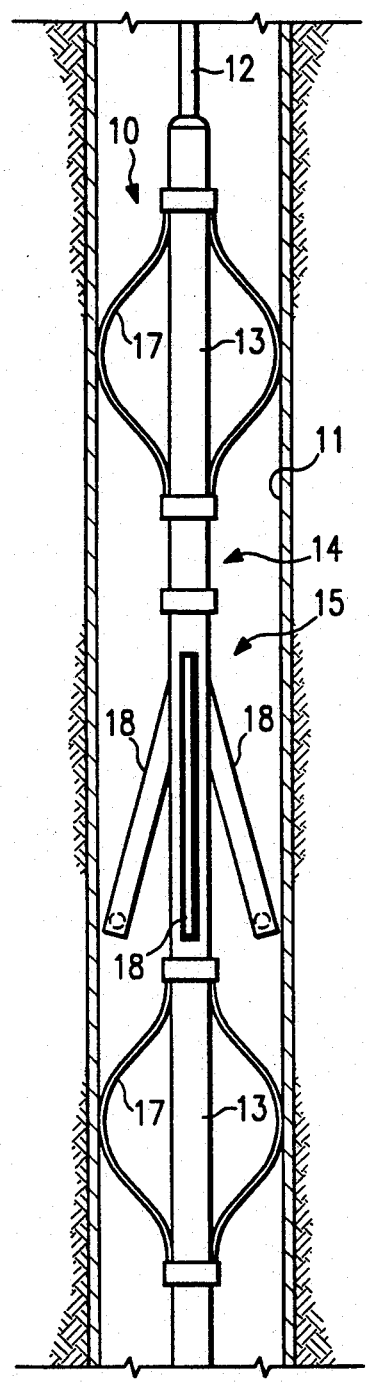
FIG. 1 is a perspective, partly in section, of the present downhole tool within a wellbore.
Figure 2:
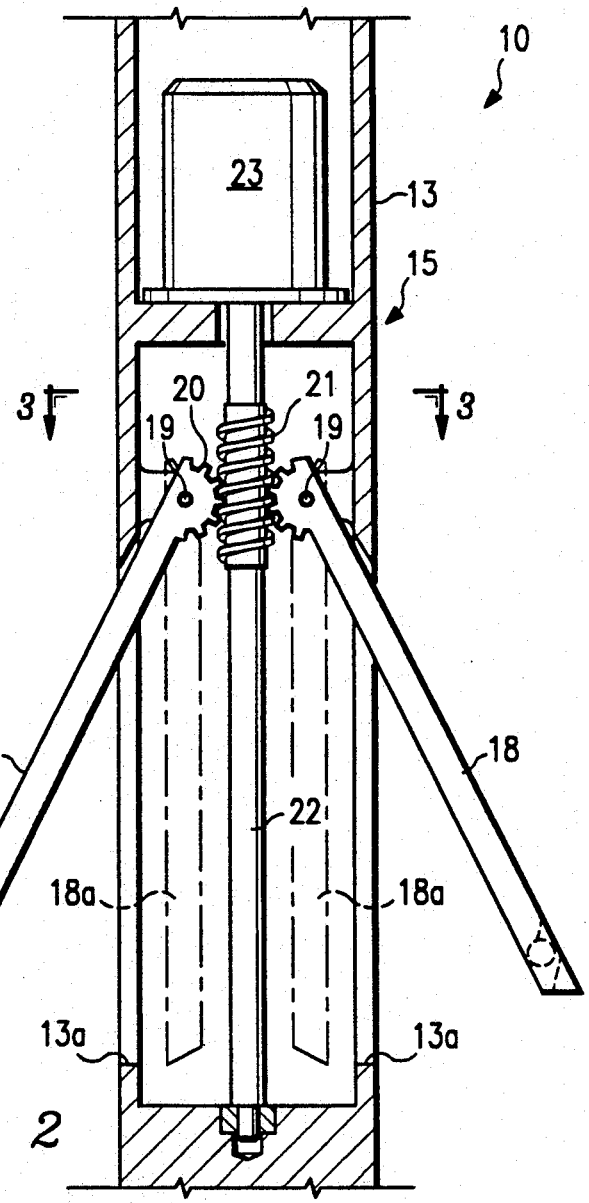
FIG. 2 is an enlarged elevational view, partly in section, of the sensing section of the downhole tool of FIG. 1.

Referring more particularly to the drawings, FIG. 1 illustrates a downhole wellbore tool 10 in accordance with the present invention as it is positioned in the flowstream of cased wellbore 11. Tool 10, as illustrated in FIGS. 1 and 2, is adapted to be positioned and operated by a "wire-line" 12 (e.g., an armored logging cable comprised of several separate conductors, not shown) and is comprised of a housing 13 having an electronic section 14 and a sensor section 15. Centralizers 17 are mounted along housing 13 to center tool 10 within wellbore 11 as will be understood in the art.

Figure 3:
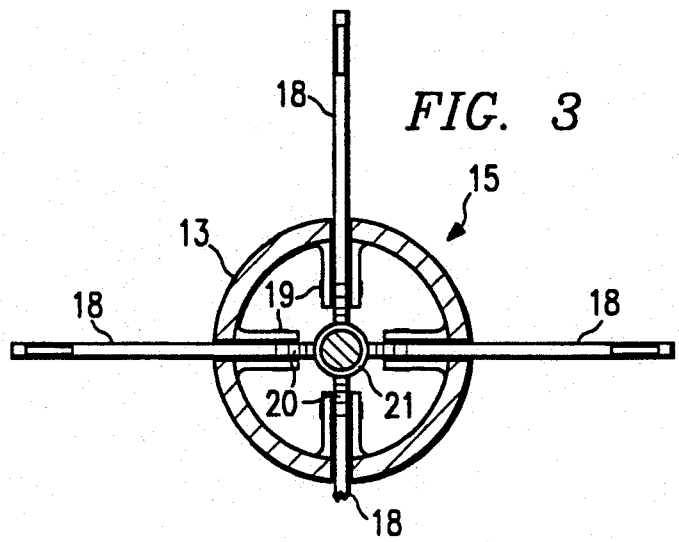
FIG. 3 is a sectional view of the downhole tool taken along line 3—3 of FIG. 2.

Referring now to FIGS. 2-3, sensor section 15 is comprised of a plurality (four shown in FIG. 3) of extendable, elongated arms 18 which are pivotably mounted in housing 13 by shafts or pins 19. Each arm 18 is extendable between its retracted position (dotted lines 18a in FIG. 2) and its extended position (solid lines in FIG. 2) through window 13a in housing 13. A wide variety of means can be used to move the arms between their relative retracted and extended positions.

For example, as illustrated, each arm 18 has a gear 20 on its inner end which cooperates with worm gear 21 on shaft 22. Shaft 22 is rotated in one direction by reversible, electric motor 23 to extend the arm and is rotated in the opposite direction to retract the arm, as will be understood in the art. Both the necessary commands and power are supplied to the motor 23 through appropriate conductors (not shown) in cable 12. Other means which can be used in place of the illustrated worm gear arrangement include a screw and nut-follower arrangement, hydraulically-actuated linkages, etc.. While FIGS. 2 and 3 illustrate a tool 10 which has four arms 18 radially spaced 90° from each other around housing 13, more or less arms 18 can be used depending on a particular situation, e.g. see FIGS. 7A and 8A.

In accordance with the present invention, sensors are carried at or near the outer ends of each of the arms 18 whereby the sensors will be deployed out from the tool body or housing into the flow through the wellbore. Each sensor will measure a property or parameter of the flow at its respective point in the wellbore. From these measurements, it is possible to construct a cross-sectional map or image at each instant of the measured fluid property.

Figure 4:
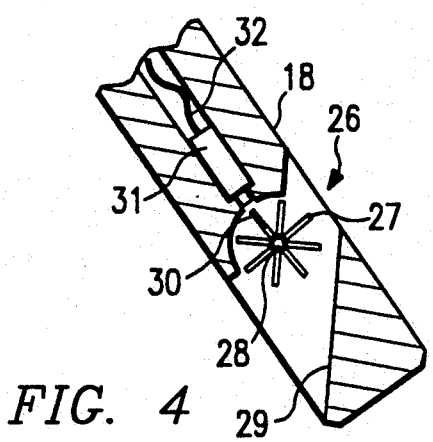
FIG. 4 is a sectional view of the outer end of an extendable arm of the present tool showing a flow-sensing means.
Figure 5:
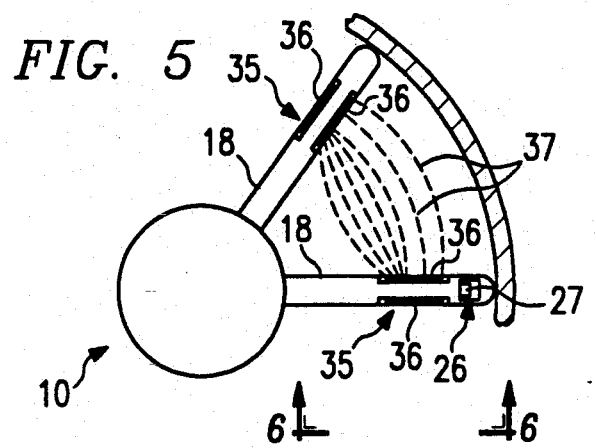
FIG. 5 is an partial plan view of a portion of the present tool sensing the capacitance of the fluids in a wellbore.

Various types of sensors can be used either alone or in combination on each arm 18. For example, FIG. 4 illustrates a flow sensor 26. As shown, flow sensor 26 is preferably comprised of a "paddle-wheel" flow sensor 27 which is rotatably mounted on axle 28 which is journalled within passage 29 through arm 18. As will be understood in the art, paddle-wheel sensors 27 include a magnetic element 30 carried by at least one of the paddles or spokes of the wheel which, in turn, is sensed by magnetic detector unit 31 which is embedded or otherwise positioned within arm 18. Whenever flow causes wheel 27 to rotate, detector unit 31 senses element 30 each time it passes and generates a signal indicative of the revolutions per minute of the wheel. This signal is sent to electronic section 14 in tool 10 through leads 32 where it is processed and/or transmitted to the surface through cable 12 for further processing. In addition to the quantitative information that is provided by the plurality of flow sensor 26, it is also possible to determine from the multiple readings when flow is faster on one side of the wellbore than another, etc.

Other sensors may also be carried by extendable arms 18 of tool 10. FIGS. 5-8 illustrate a downhole tool 10 having a capacitance sensor 35 mounted at or near the outer end of each arm 18 which can be used to determine water hold-up (i.e. the volume fraction of water present in downhole wellbore fluids). Electrodes 36 of sensor 35 are mounted on either side of the arm 18 and act as capacitor plates in measuring capacitance between facing electrodes on adjacent arms (represented by the dotted lines 37 in FIG. 5). The capacitance measured by each electrodes 36 is fed through its respective lead 38 (FIG. 6) to electronic section 14 where the signals are processed and/or transmitted to the surface through cable 12. Capacitance measuring circuits (not shown) can be conventional tank circuits which oscillate at a frequency proportional to the capacitance.

The measured capacitance between facing plates on adjacent arms is related to the dielectric permittivity in the volume between adjacent arms 18. As long as oil or gas is the external continuous phase in this volume, the permittivity will vary with the water content. Since measurements of capacitance are made in several sectors around the tool in the wellbore, a cross-sectional image of water content can be obtained, see FIGS. 7A, 7B and FIGS. 8A, 8B.

Figure 7A:
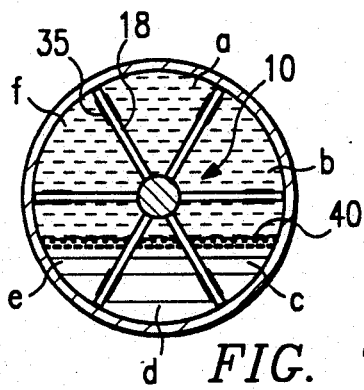
FIG. 7A is a sectional plan view of an embodiment of the present invention when submerged in wellbore fluids.
Figure 6:
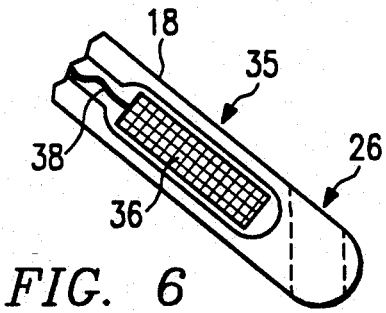
FIG. 6 is a sectional view taken along line 6—6 of FIG. 5.
Figure 7B:
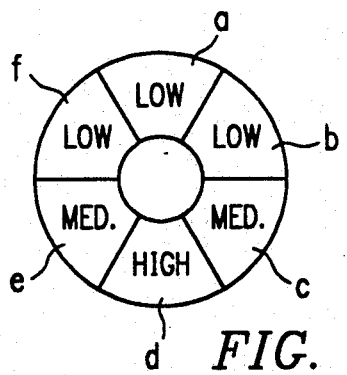
FIG. 7B is a graphic representation of the relative capacitances valves measured by the tool of FIG. 7A.

In FIG. 7A, a tool 10 having capacitance sensors 30 mounted on six extendable arms 18 is positioned within a horizontal wellbore 11. The arms 18 effectively divided the wellbore into six radial sectors a-f. As illustrated in FIG. 7A, the well fluids at that point in the wellbore below interface 40 is substantially water and above interface 40 is substantially oil and/or gas. From the capacitance readings made by the respective sensors 35 on tool 10, the profile of FIG. 7B is provided. It will be noted that the stratified flow as illustrated in FIG. 7A, produces high capacitance in only sector "d" (FIG. 7B) while recording medium capacitances in sectors "c" and "e" and low capacitances in all of the other sectors thereby producing an accurate portrayal of the actual fluid composition at that point.

Figure 8A:
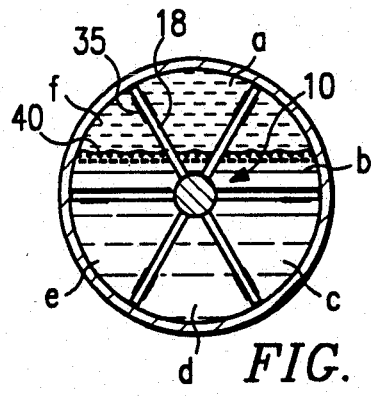
FIG. 8A is a sectional plan view of an embodiment of the present invention when submerged in wellbore fluids.

In FIG. 8A, the tool 10 is positioned in a horizontal wellbore 11 wherein the water-oil interface 40 is above that represented in FIG. 7A. Accordingly, the readings from sensors 30 in FIG. 8A will record high capacitances in sectors "c", "d", and "e"; medium capacitance in sectors "b" and "f", and low capacitance in sector "a" which produces the fluid profile shown in FIG. 8B. The capacitance sensor 35 may be used separately on an arm 18 of tool 10 or it may be used in combination with other sensors, e.g. flow sensor 26 (see FIGS. 5 and 6). Of course, each sensor would have its own respective lead to communicate its signal to the electronic section 14 of the tool.

Figure 9:
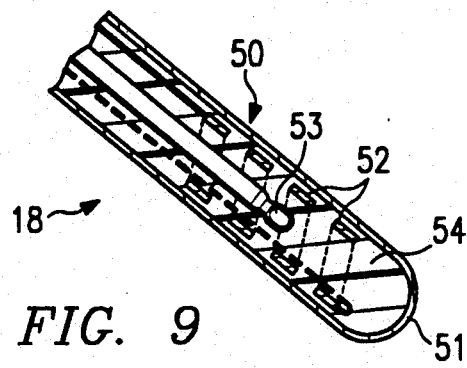
FIG. 9 is a sectional view of another arm used in the present invention having a heat sensing means thereon.
Figure 8B:
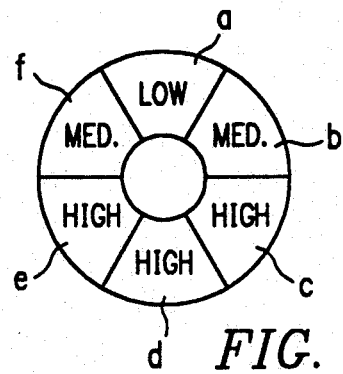
FIG. 8B is a graphic representation of the relative capacitances valves measured by the tool of FIG. 8A.

Another type of sensor which can be especially useful either singly or in combination with a flow sensor 27 is thermal probe 50 (FIG. 9). Heat sensor 50 is mounted at or near the outer end of arm 18 is comprised of a thin sheath 51 which is exposed to flow with a heating element, e.g. strip heating coil 52 and a thermometer (e.g. thermistor or thermocouple junction 53) positioned inside A cast epoxy 54 surrounds the inner elements and fills the sheath 51. Given a constant heat flow from heater 52, the temperature at the thermometer 53 is related to the heat capacity and flow rate of the fluid being measured. From a known flowrate, the heat capacity can be inferred. A gas phase will generally tend to have a much lower heat capacity than liquid phases, thus giving a good indication of the gas content of the fluid.

To make such measurements, it is preferable to deploy two or more types of sensors, either on each arm, or on nearby sets of arms. A set of capacitance sensors together with a set of flow sensors will give the cross-sectional distributions of water and flowrate. Another set of sensors to detect gas will allow a relatively complete determination of the multiphase flow pattern in a particular wellbore.

In operation, tool 10 is normally positioned in wellbore 11 in its retracted position (dotted lines 18a in FIG. 2) at a point at which the flow parameters or properties are to be measured. Motor 23 is actuated to rotate worm gear 21 to extend arms 18 into the wellbore whereby the sensors carried by the arms can make their respective measurements. Tool 10 may be maintained in one position so that the flow parameters may be recorded for a sufficiently long time to allow averaging of the chaotic flow patterns common for most multiphase flow in deviated wells. In this way, an accurate determination of the net flow of the various phases past the tool position will be possible. Additionally, more than one array or set of extendable arms may be positioned at various points along the axis of the tool 10, allowing a 3-dimensional image of the flow pattern to be determined. Further, correlations between data obtained at various locations will allow improved estimates of flow velocity of the various phases in the wellbore.

While tool 10 has been described as being positioned and operated on a wire-line, it should be recognized that tool 10 can also be adapted to be run and operated on a tubing string, preferably on a commercially-available "coiled tubing" having appropriate electrical conduits therein. Further, other types of measurements can also be made by the present multiarm tool. For example, pressure, gradiomanometer, or gamma-ray density measurements can be made at several azimuthal positions as well by using the appropriate sensor or sensors on the arms 18 of the tool 10.

What is claimed is:

1. A downhole tool adapted to be positioned into a wellbore for measuring the flow velocity of a flowstream in said wellbore said tool comprising:
    a housing;
    a plurality of elongated arms radially spaced around said housing, each arm having an inner end and an outer end;
    means for pivotably mounting the inner end of each arm in said housing;
    a sensor for sensing the flow velocity of the flowstream carried on each of said arms near its respective outer end and
    means for rotating said arms about their respective pivots to extend said sensor laterally from said housing into said flowstream without substantially restricting or redirecting said flowstream.

2. The tool of claim 1 wherein said means for rotating said arms comprises:
    a gear on said inner end of said arm;
    a worm gear adapted to cooperate with said gear; and
    a motor to drive said worm gear.

3. The tool of claim 1 including:
    a second sensor carried by each of said arms near its outer end.

4. The tool of claim 3 wherein said second sensor comprises;
    a sensor mounted on each of said arms for measuring the capacitance of the fluids which flow between two adjacent arms.

* * * * *